United States Patent [19]

Salee

[11] Patent Number: 5,630,961

[45] Date of Patent: May 20, 1997

[54] MICROWAVE-ACTIVATED MIXED-POWDER THERMAL STORAGE MATERIAL; AND METHOD

[75] Inventor: Gideon Salee, Columbus, Ohio

[73] Assignee: ThermaStor Technologies, Ltd., Columbus, Ohio

[21] Appl. No.: 438,443

[22] Filed: May 10, 1995

Related U.S. Application Data

[63] Continuation-in-part of Ser. No. 124,931, Sep. 21, 1993, Pat. No. 5,424,519.
[51] Int. Cl.⁶ .................................. H05B 6/80; A61F 7/00
[52] U.S. Cl. ........................... 219/759; 126/204; 607/101; 607/114; 607/108
[58] Field of Search ...................... 219/759, 730; 607/96, 101, 102, 108, 109, 110, 111, 112, 114; 126/204; 252/71

[56] References Cited

U.S. PATENT DOCUMENTS

| | | | |
|---|---|---|---|
| 4,849,593 | 7/1989 | Hughes et al. | 219/759 |
| 5,070,223 | 12/1991 | Colasante | 219/759 |
| 5,241,149 | 8/1993 | Watanabe et al. | |
| 5,300,105 | 4/1994 | Owens | 607/114 |
| 5,424,519 | 6/1995 | Salee | 219/759 |

*Primary Examiner*—Philip H. Leung
*Attorney, Agent, or Firm*—Porter, Wright, Morris & Arthur

[57] ABSTRACT

A thermal storage composition activated by exposure to microwave energy is provided. The thermal storage composition preferably comprises a mixture of at least two impregnated powders where a first powder is calcium silicate impregnated with a microwave-sensitive material, and a second powder is calcium silicate impregnated with a phase-change material to provide a free-flowing powder; the thermal storage mixture may be utilized in a container, to provide a thermal storage construction (heating construction) comprising a seat cushion having a thermal storage unit therein; further, a process of storing thermal energy for release over an extended period of time is described.

20 Claims, 2 Drawing Sheets

MICROWAVE-ACTIVATED MIXED-POWDER THERMAL STORAGE MATERIAL; AND METHOD

This application is a continuation-in-part of U.S. Ser. No. 08/124,931, filed Sep. 21, 1993, now U.S. Pat. No. 5,424,519.

The present application is related to patent application Ser. No. 08/438,442, filed by Gideon Salee on May. 10, 1995, Gideon Salee, the text of which is incorporated by reference as if completely rewritten herein.

FIELD OF THE INVENTION

The present invention relates to microwave-activated thermal storage compositions and materials for thermal storage units. In particular, the invention concerns arrangements which are activated or heated through exposure to microwave energy and which possess significant thermal storage ability and provide an advantageously slow release of heat over an extended period of time. Principles according to the present invention may be utilized, for example, in thermal seat cushions, foot and hand warmers, body warmers, and as warmth extenders for foods. Also according to the present invention, methods relating to preparation and use of such arrangements are presented. Typically, the invention includes materials where free-flowing powders of calcium silicate are obtained that have phase-change materials and microwave-sensitive materials impregnated into different powder particles so as to be a mixture of powders.

BACKGROUND OF THE INVENTION

Thermal storage arrangements (whether heated by exposure to microwave energy or otherwise) have been widely used for a variety of purposes. Those which are activated by microwave energy have been used for various heating applications. One such arrangement, U.S. Pat. No. 5,211,949 to Salyer, utilizes as a thermal storage material a silica powder with a phase-change material. The material is claimed to be a free-flowing powder when the particle size is between 0.007 and 0.07 microns in diameter above and below the melting temperature of the phase-change material.

Other arrangements where materials have been combined with a powder include U.S. Pat. No. 4,008,170 to Allen, where silica powder has been combined with up to 9 parts by weight water. The water/silica powder is used for cooling or as a source of water.

In U.S. Pat. No. 4,253,983, Blanie discloses paraffin compositions having improved heat reservoir properties. The disclosed paraffin compositions include paraffin combined with two different fillers so as to improve thermal conductivity and plasticity.

The present invention provides for a simple system for providing stored heat that has improved safety and handleability.

SUMMARY OF THE INVENTION

The invention typically includes a thermal storage composition activatable by exposure to microwave energy, the composition including a mixture of two powders, one powder comprising calcium silicate impregnated with a microwave-sensitive material and the other powder comprising calcium silicate impregnated with a phase-change material. The thermal storage composition preferably is a free-flowing impregnated powder. Preferably, the phase-change material has a melting point below the temperature to which the microwave-sensitive material is heated during use. The preferred melting point of the phase-change material is at least 30° C., and particularly within the range of 35° C. –65° C. Preferred phase-change materials include organic waxes, particularly paraffin wax, beeswax, candelilla wax, carnauba wax, cotton wax, wool wax, montan wax, and mixtures thereof. A preferred microwave-sensitive material is a low volatility, microwave-sensitive glycol. In a preferred embodiment of the thermal storage composition, the phase-change material includes paraffin wax and the microwave-sensitive material includes a microwave-sensitive glycol, water or a mixture thereof, and particularly dipropylene glycol, diethylene glycol, higher oligomers of propylene or ethylene glycol, water, or mixtures thereof.

Another embodiment of the invention includes a process for producing a thermal storage composition which includes a first step of mixing a microwave-sensitive material or a phase-change material with a first calcium silicate powder, at a temperature and in an amount adapted to impregnate the powder with the microwave sensitive material or phase-change material, to yield a free-flowing powder; a second step of mixing the microwave sensitive or phase-change material not selected in the first step with a second calcium silicate power, at a temperature and in an amount adapted to impregnate the second powder with the microwave-sensitive or phase-change material, to yield a free-flowing powder; and a third step of mixing the powders obtained from the first two steps to yield a free-flowing mixed powder.

A further embodiment of the invention includes a thermal storage unit which is activated by exposure to microwave energy. The thermal storage unit includes a microwave-transparent container; and, a thermal storage composition enclosed within the container, the thermal storage composition including a mixture of a first powder comprising calcium silicate impregnated with a microwave-sensitive material and a second powder comprising calcium silicate impregnated with a phase-change material. The thermal storage composition typically is a free-flowing powder. In one embodiment, the microwave-sensitive material of the thermal storage composition includes water and the phase-change material includes paraffin wax. The container typically is a flexible pouch.

Yet another embodiment of the invention includes a heating construction including a microwave-transparent outer cover and a thermal storage unit activatable by exposure to microwave energy and positioned within the outer cover. The thermal storage unit typically includes a microwave-transparent container and a thermal storage composition within the container, the thermal storage composition including a mixture of a first powder comprising calcium silicate impregnated with a microwave-sensitive material and a second powder comprising calcium silicate impregnated with a phase-change material. The thermal storage composition typically is a free-flowing impregnated powder. In one embodiment of the heating construction, the microwave-sensitive material of the thermal storage composition includes water and the phase-change material includes paraffin wax. The microwave-transparent outer cover typically is a seat cushion.

In still another embodiment of the invention, a process of storing thermal energy for release over an extended period of time includes the step of exposing a thermal storage composition to microwave energy. The thermal storage composition comprises a mixture of a first powder comprising calcium silicate impregnated with a microwave-sensitive material and a second powder comprising calcium silicate impregnated with a phase-change material. The step of exposing the thermal storage composition to microwave energy includes exposing the thermal storage composition to microwave energy of appropriate power and for a sufficient period of time to heat the thermal storage composition to a temperature above the melting point of the phase-change material and to melt the phase-change material.

DETAILED DESCRIPTION OF THE INVENTION

The principles of the present invention, with respect to thermal storage units and arrangements, may be applied in a variety of systems. The systems may be used, for example, as sources of warmth for humans, for example, as seat cushions, shoe inserts, foot warmers, hand warmers, etc. The principles of the present invention may, however, be applied in a variety of other systems as well, for example, to provide a thermal blanket for food containers or other items to be kept warm. In the figures, a thermal storage unit according to the present invention is shown in the embodiment of a seat cushion. From the general principles described herein, application in a variety of other arrangements will be apparent.

Figure 1:
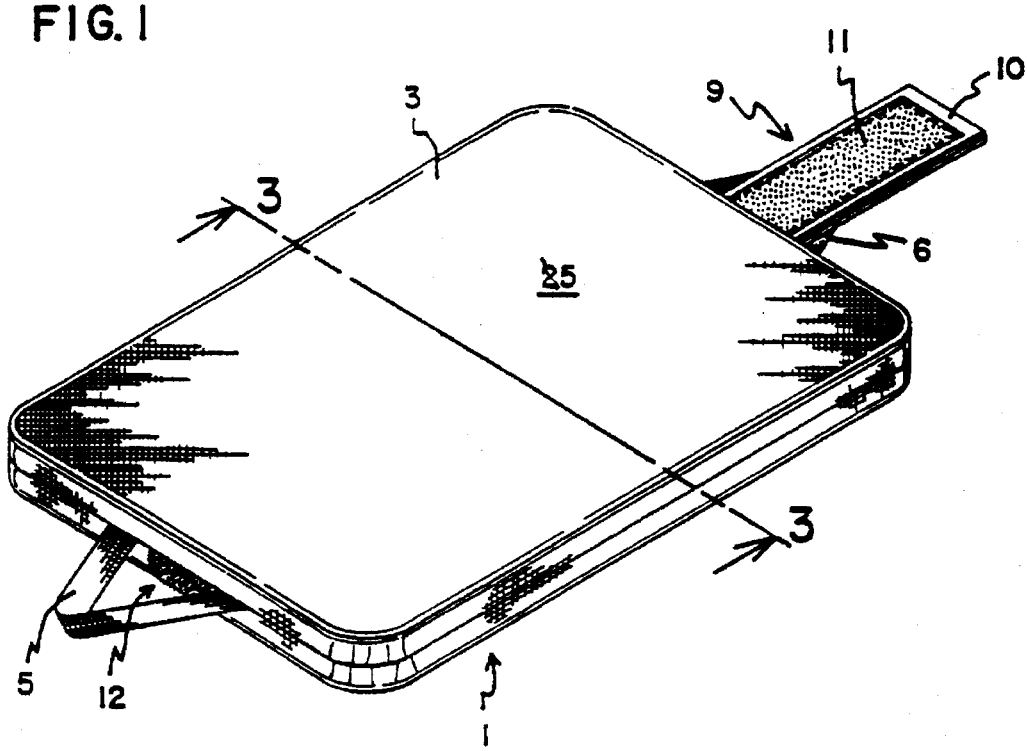
FIG. 1 is a perspective view of a cushion according to the present invention.

Reference numeral 1, FIG. 1, generally designates an arrangement or heating construction according to the present invention, including a thermal storage unit 20 therein. Arrangement 1, FIG. 1, generally comprises a flexible seat cushion 3. The cushion 3 depicted is sufficiently flexible to be folded, and includes carrying handles 5 and 6, comprising, for example, polypropylene webbing or similar material. A closure arrangement to retain the cushion 3 folded, when desired, is indicated generally at 9. The closure arrangement 9 depicted comprises a strap 10 including a first member 11 of a hook and loop closure system thereon. A second member 12 of the hook and loop closure system is indicated on, and underneath, the underside of the cushion 3, at 12. Thus, when cushion 3 is folded, strap 10 can be folded to engage section 11 with 12 to retain the cushion 3 in a closed orientation. The hook and loop closure system may comprise, for example, the well-known system sold under the mark VELCRO®. Alternative closure arrangements, for example snaps, buckles, buttons or ties, may, of course, be used.

Figure 3:
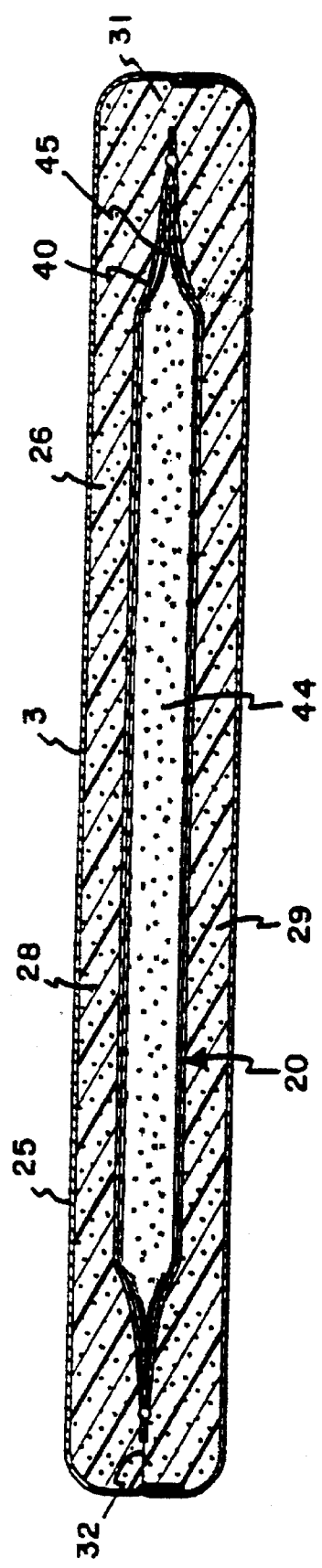
FIG. 3 is a cross-sectional view along line 3—3 of FIG. 1.

Cushion 3 includes therein, according to the present invention, a thermal storage unit 20, FIG. 3. In operation, cushion 3 is exposed to microwave energy. After several minutes of exposure to the microwave energy, for example in a microwave oven, the cushion 3 will become relatively warm (a temperature of the thermal storage unit of around 35° C.–60° C. being typical). This effect is accomplished because cushion 3 includes, embedded therein, a thermal storage unit 20 according to the present invention.

In FIG. 3, a cross-sectional view of cushion 3 is depicted. Cushion 3 includes an outer cover or sheath 25, which encloses the various inner components. The sheath 25 may comprise a fabric, for example, a fire retardant nylon or more preferably a polyolefin. The inner components include foam pad 26 which surrounds thermal storage unit 20. More specifically, in the embodiment shown foam pad 26 includes first and second pads or walls 28 and 29, with thermal storage unit 20 positioned therebetween. Along edge 31, walls 28 and 29 may be integral with one another, i.e., they are merged continuously with no interface or seam. Along with at least part of edge 32, on the other hand, walls 28 and 29 can be separated, for insertion of thermal storage unit 20 during assembly. In preferred embodiments, foam pad 26 comprises a sheet of foam slit to form an envelope, such that thermal storage unit 20 can be readily inserted therein during assembly. Alternatively, foam pad 26 may comprise a sheet of foam folded, or foam pad 26 may comprise two pads arranged to form a sandwich type construction such that thermal storage unit 20 can be readily inserted therein during assembly.

Still referring to FIG. 3, thermal storage unit 20 comprises an outer pouch 40 having sealed therein a thermal storage composition comprising an impregnated powder 44. The powder useful for impregnation most preferably comprises a powder such as a calcium silicate powder. In the particular embodiment shown, the impregnated powder 44 is calcium silicate powder impregnated with a microwave-sensitive material and a phase-change material, wherein a first powder portion is impregnated with the microwave-sensitive material and a second powder portion is impregnated with the phase-change material. Typically the percentage of powder material impregnated with the phase-change material will be much larger than the percentage impregnated with microwave-sensitive material.

As used herein the term "impregnation" includes the adsorption and/or absorption of microwave-sensitive and phase-change materials to powder particles. Similarly, the term "adsorb" includes the known phenomena of "adsorption" and "absorption" of liquid with the powder particles. This is because either one or both phenomena may be present in any particular impregnated powder particle; that is, the same particle may have material adsorbed to its surface as well as have material absorbed within pores or spaces of the particle. Further, not wishing to be bound by the particular explanation of what is occurring in terms of absorption or absorption of the materials to the powders, the important consideration is that the phase-change materials and the microwave-sensitive materials are sufficiently "held" by the powder that a free-flowing impregnated powder is obtained at the temperatures of intended use.

Figure 2:
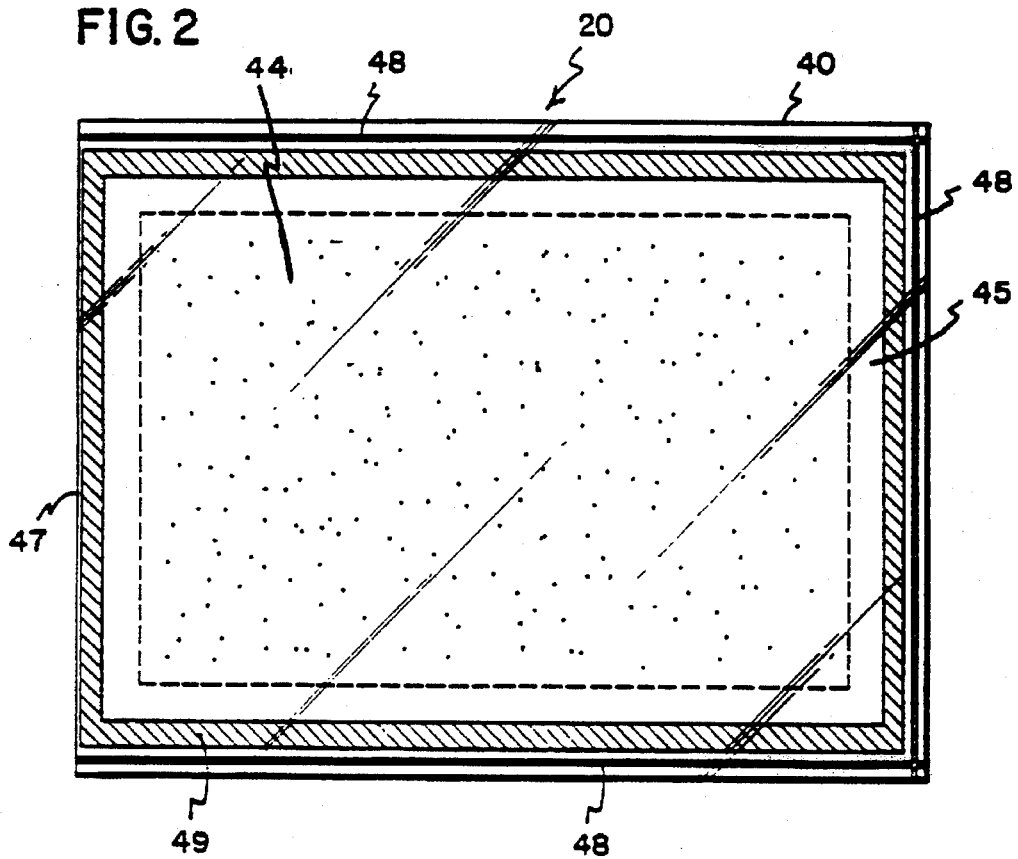
FIG. 2 is a top plan view of a thermal storage unit according to the present invention which may, for example, be utilized in the arrangement of FIG. 1.

A top plan view of the thermal storage unit 20 is depicted in FIG. 2. For the embodiment shown in FIG. 2, thermal storage unit 20 includes outer pouch 40, and a second inner pouch 45. That is, outer pouch 40 completely encloses inner pouch 45. Alternately stated, thermal storage unit 20 can be a "double bag" arrangement, with outer pouch 40 sealing a second inner pouch 45 for security. This is advantageous, since material received within inner pouch 45 will, upon exposure to microwave energy, become relatively hot; and, material enclosed within inner pouch 45 is a free-flowing powder. Thus, should seals in inner pouch 45 fail, or should a failure or puncture occur in inner pouch 45, outer pouch 40 will inhibit leakage of powder. An important consideration for the outer and inner pouches 40 and 45 is that the pouch material melts at temperatures in excess of those produced on heating the powder in a microwave oven. A high melt temperature is more important than in the embodiment revealed in the copending parent application, since higher localized temperatures are expected to be encountered with the powder used herein than with the liquid version.

For the arrangement shown in FIG. 2, outer pouch 40 comprises a film folded along fold line 47 with inner pouch 45 positioned therein. Edge seals 48 may comprise a variety of types of seals, for example, heat seals or adhesive seals. For the preferred arrangement described and shown, preferably outer pouch 40 is formed from a heat sealable film, and edge seals 48 comprise heat seals, formed in a conventional manner. Optional inner pouch 45 also preferably comprises a heat-sealable film. For the arrangement shown in FIG. 2, inner pouch 45, not shown in detail, includes peripheral heat seals 49.

In a further embodiment the inner pouch 45 can be dispensed with and the impregnated powder 44 freely distributed in the inner space of the outer pouch 40. In this embodiment the impregnated powder 44 would be held in place only by outer pouch 40. This arrangement is also acceptable as the impregnated powder 44 will not escape as readily as a liquid would. In this respect, in a yet further embodiment of the invention, the outer pouch and/or inner pouch 45 can be of a gas permeable material. Gas permeability would allow volatile components to escape should the thermal storage unit be overheated in the microwave oven by exposing it to microwave radiation to high power for too long a period. As such this further embodiment offers a significant safety improvement as overheating would tend to produce hot gases that could cause an impermeable pouch to burst should the internal pressures become too high. This possibility is present especially with the embodiment where the components in the pouch are relatively low boiling liquids such as water. On the other hand, initially water and similar volatile materials will contribute to more even distribution of temperature in the system by mass transfer i.e., volatilization at hot spots and condensation in cooler areas.

In an embodiment where the microwave-sensitive material is water, it is expected that the volatile gas driven off on overheating will be water vapor. A permeable sheath and pouch cover would allow water vapor driven off the powder by overheating to escape. Then, ambient levels of water vapor in the environment can penetrate to the impregnated powder 44 and allow the powder to readsorb any water driven off by excess heating. This latter point is especially true for calcium silicate which will readily adsorb ambient water vapor from the air. Thus in this respect a preferred powder material has at least some hygroscopic characteristics for adsorbing water from the atmosphere.

Referring now to FIG. 3, as previously-indicated, impregnated powder 44 is sealed within either (1) both outer pouch 40 and inner pouch 45 or (2) only outer pouch 40. In preferred embodiments, impregnated powder 44 provides three basic operations in use: (1) it is a free-flowing powder and formable, and thus is comfortable to the user of the cushion 3; (2) it easily spreads over a greater surface area if desired; and (3) it has good thermal characteristics such as low levels of hot spots and acceptable heat transfer from the microwave-sensitive material to the phase-change material, on heating in a microwave oven.

The impregnated powder 44 comprises a mixture of materials to serve two primary purposes in a preferred manner: it is readily heated up upon exposure to microwave energy; and, it will dissipate heat therefrom, in cooling back to ambient, at least in part by a phase transfer of a material impregnated in the powder. By "readily heated up upon exposure to microwave energy" in this context, is meant that it will heat to a selected or preferred temperature, for example, typically to at least 30° C. to 30° C.–90° C., and usually to a selected point within the range of about 30° C.–65° C., upon exposure to microwave energy in a 700 to 1000 watt microwave oven, for a period of 3 to 15 minutes or so.

Preferred operation of the thermal storage unit 20 turns upon utilization of preferred materials. Details with respect to these materials are as follows.

1. The Powder

The powder or powders useful for impregnation are any that provide sufficient adsorption/and or absorption to the oil phase or phase change material and the microwave-sensitive material. Preferred are powders with large surface areas compared to the volume of the powder particles. The powder particles themselves will preferably be almost completely or substantially insensitive to microwave radiation relative to the microwave-sensitive material.

Typically a wide range of powder particle sizes are useful with the invention. Preferred particle sizes are above about 1 micron. More preferred are particles sizes of above about 1 micron to 100 microns. Most preferred are particle sizes of about 10 to 80 microns. An important consideration is that the particles sizes selected not interfere with a high loading in the impregnation and retention of microwave-sensitive and phase-change materials on the powder. Another consideration is that larger particle sizes will reduce dust generation during the preparation of the powder.

In this regard, a most preferred powder of the type herein described is calcium silicate.

2. Preparation of the Impregnated Powder

Powder mixtures, used in preparing thermal storage compositions according to the present invention, comprise first and second materials impregnated onto separate powder particles. The wax or oil phase, at lower temperatures (e.g., 25° C.), is solid or liquid and impregnated to a first calcium silicate powder and the wax or oil phase (i.e., solid phase), after the arrangement has been sufficiently heated up upon exposure to microwave energy, becomes a liquid and remains impregnated to the calcium silicate. Herein the terms "wax" and "oil" are used interchangeably to refer to the phase-change material (microwave-insensitive phase) which is impregnated to the powder. In typical applications, the "oil phase" or "phase-change material" in the mixture should comprise a material having a melting point somewhere within the range of about 0° C. to 100° C., more preferably about 30° C.–90° C., and most preferably 30° C.–65° C.

Preferably, the "oil phase" is a material which is not microwave sensitive. Rather, in typical applications, the oil phase or solid phase impregnated on a majority of the particles of the impregnated powder 44 is heated up and melted by thermal transfer from the microwave-sensitive material impregnated to other powder particles. In typical applications, oil phase or phase change material, impregnated to some particles of the impregnated powder 44, is heated up and/or melted by thermal transfer from a microwave-sensitive material that is impregnated to other powder particles that are mixed therewith. The microwave-sensitive material may be a liquid, a solid, or may itself undergo phase changes at the temperatures at which the invention is used (if the temperature change is large enough); however, the microwave-sensitive material is not intended to and will ordinarily not undergo phase changes.

Principal characteristics to be considered in selecting the phase-change material for the "oil phase" concern the following. The melting point of the phase-change material should be a melting point at a temperature satisfactory for the use to which the thermal storage composition is to be placed. For example, if the thermal storage composition is utilized as a part of a thermal storage unit for a seat cushion 3 (for example, in an arrangement as shown in FIGS. 1–3) it will be preferred that the phase-change material be chosen to have a melting point of at least 40° C., preferably about 50° C.–60° C., typically and most preferably at around 50° C.–55° C. Such a temperature is relatively warm, but suitable for an internal storage unit within a seat cushion.

On the other hand, if the thermal storage composition is being utilized in a system more likely to come into closer contact with exposed skin, and relatively sensitive areas of the body, it may be desirable to utilize as the "oil phase", a material having a lower melting point. For example, if the thermal storage composition is utilized as part of a thermal storage unit for a hand warmer, or foot warmer, for bare hands or bare feet, a melting point on the order of about 30° C.–40° C. may be preferred, since higher temperatures may be uncomfortable for the user.

Other factors to be considered in the selection of the material for the "phase-change material" or "oil phase", concern heat of fusion (or latent heat of melting). In general, the greater the heat of fusion, the greater the amount of heat given off, per unit weight, as the phase-change material cools and solidified, and thus, better the material will operate as a thermal storage material, since, after having been heated to liquid, a longer period of time, with greater energy lost, will be achieved before the phase-change material returns to a solid. Alternatively, the greater the heat of fusion, the more energy or heat the phase-change material will be able to store per unit weight, during the initial heating up in the microwave oven.

Another factor to be considered in selecting the material for the phase-change material is the ability to form a stable impregnation with the powder particles. In general, materials that can relatively readily impregnate with the calcium silicate powder over a temperature range on the order of about 0° C.–90° C., will be preferred. It is anticipated that, for reasons stated hereinbelow, the typical microwave-sensitive material will be dipropylene glycol and/or water. The material for the phase-change material and microwave-sensitive material should not chemically react with each other and should not readily separate from the powder, should the thermal storage unit 20 be subjected to relatively hot or cold temperatures, with melting, freezing, or some other form of inducement to separation from the powder.

Paraffin wax is a preferred material for use in compositions for thermal storage units according to the present invention, especially when the thermal storage unit is utilized as part of a seat cushion. Paraffin wax is a mixture of solid hydrocarbons having the general formula $C_nC_{2n+2}$ and typically has a melting point somewhere within the range of 45° C.–60° C. Particular waxes can be selected, for preferred melting points. Thus, a particular paraffin wax can be selected and obtained with a melting point of about 50° C.–57° C., i.e., 53° C., if desired. Paraffin waxes in general exhibit melting points over the preferred ranges for utilization with systems, according to the present invention; they readily impregnate with calcium silicate powder; they are relatively non-toxic; they exhibit desirable heat-storage capabilities; and they are relatively inexpensive and easy to obtain. It is foreseen that derivatives of paraffin wax, such as alkylated paraffins, having similar melting point ranges, may also be used. The term "paraffin wax" as used herein, is meant to include not only materials according to the general formula $C_nH_{2n+2}$, but also modified waxes such as alkylated paraffin wax derivatives of such materials and similar compounds. Examples include long chain alcohols (e.g., stearyl alcohol and cetyl alcohol), and long chain saturated fatty acids (e.g., capric acid, lauric acid, myristic acid, palmitic acid, stearic acid, and myristic acid) and the like.

Other usable materials in the "oil phase" and systems according to the present invention include: beeswax; (mp. 62° C.–65° C.); candelilla wax (mp. 68° C.–70° C.); carnauba wax (mp. 82° C.–85.5° C.); cotton wax; wool wax; montan wax (mp. 80° C.–86° C.); and, mixtures of waxes. A preferred paraffin wax for systems according to the present invention is a fully refined paraffin having a nominal melting point of 53° C.

The preferred microwave-sensitive material should comprise a material which readily absorbs microwave energy and converts the microwave energy to heat and, as a result, rapidly heats. Preferably water or water mixtures (such as water/alcohol, water/glycol, or water/glycerol) are used. Water, of course, is also desirable from the point of view of toxicity and cost. In some systems, aqueous solutions of various salts may be desirable for the microwave-sensitive material, for example solutions of calcium chloride, sodium chloride, aluminum sulfate, magnesium bromide or magnesium sulfate.

The phase-change materials and the microwave-sensitive materials may include adjuvants such as surfactants or emulsifiers, preservatives and/or dyes. These will be discussed in greater detail below.

In general it is the wax phase (in some embodiments it is solid at room temperature) of the mixture which performs much of the thermal storage function in powder mixtures used in thermal storage units according to the present invention. Thus, it will generally be preferred that mixtures utilized in thermal storage units according to the present invention include a relative amount, for example by weight, of microwave-insensitive-heat-storage phase (phase-change material) to microwave-active phase which reflects the least amount of microwave-sensitive material needed to heat the microwave-insensitive-heat-storage phase for the particular application. The amount of phase-change material desired for any given application will depend, of course, upon the size of the thermal storage unit needed; the length of time it is required to remain somewhat warm; and, the conditions under which it is to be used. Generally, impregnated materials for the powders comprising about 45 wt % to 95 wt % by weight phase-change material, the balance comprising microwave-sensitive material, anti-microbial agents and possibly other adjuvant, will be useful and preferred. The specifics given below for an example of a seat cushion 3 provide basic principles of operation which can be extended to many other uses.

In one typical embodiment, it is foreseen that powders according to the present invention will be prepared by (1) mixing a melt of the microwave-sensitive material together with calcium silicate powder, until all of the microwave-sensitive material has been impregnated therewith; (2) mixing a melt of the phase-change material together with other calcium silicate powder, until all of the phase-change material has been impregnated therewith; and (3) mixing desired ratios of impregnated powder from (1) and (2) to obtain the final product powder.

3. Other Adjuvants

It is foreseen that in some instances other adjuvants may be provided in the mixture. For example, preservatives may be included, to inhibit bacterial growth over the life of the thermal storage unit. For typical systems, for example involving a paraffin and water impregnated with calcium silicate powder, preservatives such as chlorobutanol; dichlorobenzyl alcohol; propylene glycol; formaldehyde; phenylmercuric acetate; benzoic acid; chloromethyl isothiazolinone; methyl isothiazolinone; dehydroacetic acid and its sodium salt; potassium sorbate; parabens; sodium pyrothione; zinc pyrothione and glutaraldehyde will be effective to accomplish this. In general, the amount of preservative should be an amount effective to achieve the desired level of resistance to biological activity. The specific formulation given hereinbelow, for a preferred arrangement utilizable as a seat cushion 3, provides further guidance with respect to this.

Other adjuvants which may be utilized in thermal storage compositions according to the present invention include dyes; antioxidants; flame retardants, etc.

4. Use of the Mixture of Impregnated Powder as a Thermal Storage Material

In use, mixtures of impregnated powders according to the present invention operate as thermal storage material, upon activation with microwave energy. In a typical use, the mixed powder is exposed to sufficient amounts of microwave energy such that the phase-change material impregnated portion of the powder is heated to a temperature above the melting point of the "oil" phase or phase-change material. In addition, if the phase-change material is not microwave sensitive, sufficient energy should be imparted to the microwave-sensitive material impregnated on one set of powder particles such that by thermal transfer (from the microwave-sensitive material containing powder to the phase-change material containing powder) that the phase-change material is melted.

Upon removal from the microwave oven, the impregnated powder 44 will be hot. It will undergo two separate steps in cooling: (1) The mass of the powder particles themselves and the mass of microwave-sensitive material impregnated with the powder particle will ordinarily undergo sensible heat loss only; and (2) The mass of phase-change material impregnated with the powder particles will undergo three periods of cooling: a period of sensible heat loss (from the original liquid phases) above the freezing point of the phase-change material; a period of latent heat loss during transition of the phase-change material from a liquid to solid (at about the phase transfer temperature thereof); and, a second sensible heat loss period below the melting point of the phase-change material.

The heat loss in the two periods of sensible heat loss will generally be controlled by the heat capacity of the original liquid phase-change material, microwave-sensitive material, and powder. For a liquid phase such as wax or water, the sensible heat loss will be relatively rapid by comparison to heat loss during the middle stage of transformation in the material from liquid to solid. During the stage of heat loss which occurs during the transformation of the phase-change material from a liquid to a solid, heat loss will be controlled by such characteristics as rate of crystallization of the phase-change material. Thus, it can be seen, that the phase-change material serves as a thermal reservoir which will act to retain the impregnated powder composition at a relatively constant, temperature, for a significant length of time, by comparison to a system which just utilizes a liquid phase.

EXAMPLES

The following examples are disclosed to further teach the practice of the invention and are not intended to limit the invention as it is delineated in the claims.

Example 1

A small amount of methylene blue was added to about 40 g of dipropylene glycol. The methylene blue was added in order to follow the dispersion of the dipropylene glycol. The mixture was shaken and heated to 70° C. in an oven for about 15 minutes. 10 g of Micro-Cel E were placed in a Brabender mixer and 24 g of the above mixture was slowly added in 2 g increments. The Micro-Cel E is a product of the Celite Corp. Lompoc, Calif., USA, and is calcium silicate powder that has a particle size distribution where 94 n % (population or number percent) of the particles are smaller than 44 μm (325 Mesh), a surface area of about 120 m²/g, and may contain up to 2 wt % crystalline silica: quartz. The material was allowed to mix for one minute between each addition. This resulted in 24.78 g of a blue fairly free-flowing powder. An additional 7.2 g of the above blend was recovered as a chunky slightly more coagulated portion of the mix. This latter material was not used. This resulted in approximately 71% impregnation of the dipropylene glycol onto the Micro-Cel E.

Example 2

A piece of Boler 941 paraffin wax (IGI Boler Inc.), having a melting point of 50° C. (122° F.) was minced with galvanized ¼" screening. Then 61.8 g of Micro-Cel E were placed in a 2 liter bottle and 115.0 g of the minced Boler 941 wax was added. The bottle was placed on a roller mill overnight to dry blend the materials. The dry-blended materials were placed in a Brabender heated to 70.5° C. (159° F.) and blended at 60 rpm. A small sample was tested and did not show any separation or melt flow.

About 153 g of the above material was further mixed for an additional 15 minutes with 7.1 g of the free-flowing powder of Example 1.

About 159 g of the mixed powders were obtained. The mixed powders contained about 62 wt % Boler 941 wax, 35 wt % Micro-Cel E, and 3 wt % dipropylene glycol.

About 120 g of the prepared mixture was placed in a plastic bag and heat sealed. The bag was heated in a 1 kw microwave oven for three minutes and reached a temperature of 70.5° C. (159° F.) with no evidence of melted wax.

Example 3

A 65 g piece of Boler 941 wax was grated and dry mixed with 35 g of Micro-Cel E by rolling in a bottle. The dry mixture was placed in a Brabender mixer for 15 minutes at 70.5° C. (159° F.) at 60 rpm. A small sample of the hot mixed powder was placed in an aluminum dish at 65.5° C.–71.1° C. (150° F. –160° F.). There was no evidence of any melted wax.

7.2 g of the powder from Example 1 was added to the hot melted mixture in the Brabender mixer and mixed for 10 more minutes at same conditions. The resulting mixture was removed hot and stored in a container. The mixture was noted to pick up moisture on standing.

Example 4

Using the same Micro-Cel E powder as in Example 1, 1.9 parts by weight grated paraffin wax (Boler 941) was impregnated on one part Micro-Cel E powder. The mixing was done in a heated sigma blade Brabender at a temperature of about 71.1° C. (160° F.) for 15 minutes at a rotational speed of 60 rpm. The product contained 65 wt % wax and was tested on a hot plate kept at 65.5° C.–71.1° C. (150° F.–160° F.). The product did not show any tendency to form a liquid melt.

In order to render the material heatable by microwave energy, the powder was mixed with a second type of powder. The second type of powder was prepared by mixing dipropylene glycol and calcium silicate at temperatures above the melting point of the dipropylene glycol. The dipropylene glycol is a low volatility microwave-sensitive glycol. The resultant second powder had a composition of about 70 wt % dipropylene glycol and 30 wt % calcium silicate.

Fifty grams of the two powders containing 4.6 wt % of dipropylene glycol were placed in a clear plastic film pouch. The pouch having the dimensions 8.9 cm by 10.8 cm (3.5 in by 4.25 in) reached 72.2° C. (162° F.) when heated in a 1000 watt microwave oven for three minutes.

5. Specific Example of a Working Embodiment

In the following description, a working example of a specific embodiment of the present invention, involving the utilization of compositions for thermal storage units in the context of a seat cushion 3, is presented. From the specifics provided, general applications of the present invention in a wide variety of systems can be foreseen and understood.

The following materials are described for use in the context of a seat cushion 3 for use by adults. The seat cushion 3 described will have outer dimensions of about 32 cm×47 cm×3 cm.

The sheath 25 for the working example described comprises a nylon fabric (preferably a rip-stop nylon). A specific, useable material is 200 denier Nylon Oxford Taffeta, No. 68295 available from Tapetex Corp., Rochester, N.Y. 14623. Preferably a material is selected which has been subjected to fire-retardant treatment. This material is utilized for the portion of the cushion 3 corresponding to sheath 25, FIG. 3.

The foam envelope, corresponding to foam pad 26, FIG. 3, comprises any conventional seat cushion foam, for example a polyurethane foam slit to form the envelope. Preferably fire-retardant foam is selected. A usable material is L32SX Foam, available from E. R. Carpenter, Templeton, Tex. 76503. The foam envelope is selected with exterior dimensions substantially corresponding to those desired for the overall construction.

The thermal storage unit 20, as indicated generally above, comprises an outer pouch 40 enclosing an optional inner pouch 45, which encloses an impregnated powder mixture as described herein. The outer pouch 40 comprises an 8 mil matte two-side vinyl available under the trade name Delta 6 from Flex-Seal Packaging of Rochester, N.Y. The dimensions of the pouch are about 30 cm×42 cm, with a 0.6 cm heat seal along the periphery thereof.

The inner pouch 45 in one embodiment preferably comprises a polymeric laminate, for example, a nylon/high density polyethylene (HDPE) polymer or a polypropylene/nylon (coated with polyvinylidene chloride) copolymer. The dimensions of the inner pouch 45 are about 28 cm×39 cm, with a 1.25 cm heat seal around the periphery thereof. For the embodiment where the pouches are permeable to gas, a nylon fabric, preferably a rip-stop nylon as specified above for the sheath 25, or more preferably a polyolefin based fabric may be used.

Received inside the inner pouch 45 (or the outer pouch 40, if only one pouch is used) are the impregnated calcium silicate powders consisting of a first powder impregnated with a phase-change material that is microwave insensitive and a second calcium silicate powder impregnated with a microwave-sensitive material. The outer and inner pouches 40 and 45 preferably comprise a material that is stable to the temperatures to which the system will be heated in use; does not hydrolyze under the conditions of use; and, is not affected by the microwave-sensitive or insensitive material impregnated with the calcium silicate powder.

The microwave-inactive-phase-change material, may comprise a mixture, by weight, as follows: paraffin wax about 99 wt % (melting point about 55° C.); preservative ucracide 250, a glutaraldehyde, available from Union Carbide, 0.1–0.2 wt %; and Proxel GLX (1,2-benzisothiazolin-3-one), 0.1–0.2 wt %; and/or an antioxidant such as BHT. Preferably the paraffin wax should have a small amount of BHT mixed therewith in order to inhibit oxidation; an amount not in excess of 1 wt % (0.1 to 1 wt %) of the paraffin wax is preferred.

For the arrangement described in the drawings, it is anticipated that about 1 to 2 kg of impregnated powder mixture would be preferred.

When the impregnated powder mixture is enclosed within a film outer or inner pouch 40 or 45 (FIG. 2), in some embodiments it may be desirable to apply some vacuum draw to the interior of the film pouch, to reduce air presence and facilitate heat transfer from one powder particle to another. However, this is not generally needed nor desired as it will reduce the ability of the powder to flow freely due to closer packing of the powders. Of course, one advantage of the closer packing due to a vacuum would be enhanced heat transfer from one powder particle to another.

The construction described is prepared for use by placement in a 700 or 750 watt microwave oven for about three minutes on each side. If simply left standing at about 5° C.–20° C., it would remain warm for about, 4 to 8 hours. The actual rate of heat loss in use will depend, of course, upon how much of the time the cushion 3 is used with a person sitting thereon; the size of the person; the ambient temperature; and related factors.

6. Alternative Applications of Principles According to the Present Invention

The specific arrangement described above, of a seat cushion 3, involves an arrangement which is intended to radiate heat from an outer surface thereof, to the exterior environment. Thus, the material chosen to enclose the thermal storage unit 20 is a material which will allow the thermal energy to pass toward an outer surface thereof, to warm the user.

It is foreseen that in alternative embodiments, thermal storage units 20 according to the present invention may be enclosed within insulating blankets or the like designed to retain heat therein. For example, such heating constructions might be utilized as hand-warming muffs or foot-warming boots or shoes. They may also be utilized, for example, as thermal blankets or the like. Alternatively, as will be appreciated by those skilled in the art, the thermal storage units 20 can also be used for keeping materials cold. By appropriate choice of melting point of the phase-change material colder temperatures can be maintained. Then by cooling the composition below the melt temperature a lower temperature will be maintained. The latter use would provide beneficial relief during hot weather, assist in food or medical storage, or provide treatment where cold compresses and the like are desired. The compositions can be kept in a regular freezer and rapidly brought to the desired application temperature for use either as a heating or cooling medium.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

What is claimed is:

1. A thermal storage composition activatable by exposure to microwave energy, said composition comprising: a mixture of, (a) a first powder comprising calcium silicate impregnated with a microwave-sensitive material; and, (b) a second powder comprising calcium silicate impregnated with a phase-change material.

2. A thermal storage composition according to claim 1 wherein: said phase-change material comprises material having a melting point below that to which said microwave-sensitive material is heated, during use.

3. A thermal storage composition according to claim 1, wherein said thermal storage composition is a free-flowing impregnated powder.

4. A thermal storage composition according to claim 1, wherein said microwave-sensitive material comprises a low volatility, microwave-sensitive glycol.

5. A thermal storage composition according to claim 4, wherein said phase-change material comprises organic wax material.

6. A thermal storage composition according to claim 1, wherein said phase-change material comprises wax selected from the group consisting essentially of: paraffin wax; beeswax; candelilla wax; carnauba wax; cotton wax; wool wax; montan wax; and, mixtures thereof.

7. A thermal storage composition according to claim 1, wherein said solid phase-change material comprises material having a melting point of at least 30° C.

8. A thermal storage composition according to claim 1, wherein said phase-change material comprises material having a melting point within the range of 35° C.–65° C.

9. A thermal storage composition according to claim 8, wherein said phase-change material comprises paraffin wax and said microwave-sensitive material is selected from the group consisting of a microwave-sensitive glycol, water or a mixture thereof.

10. A thermal storage composition according to claim 8, wherein said phase-change material comprises paraffin wax and said microwave-sensitive material is selected from the group consisting of dipropylene glycol, diethylene glycol, higher oligomers of propylene or ethylene glycol, water, or mixtures thereof.

11. A process for producing a thermal storage composition comprising:
(a) mixing a microwave-sensitive material or a phase-change material with a first calcium silicate powder, at a temperature and in an amount adapted to impregnate said powder with said microwave-sensitive material or said phase-change material, wherein a free-flowing powder is obtained;
(b) mixing microwave-sensitive or said phase-change material not selected in step (a) with a second calcium silicate powder, at a temperature and in an amount adapted to impregnate said microwave-sensitive or said phase-change material, wherein a free-flowing powder is obtained; and
(c) mixing the powders obtained from steps (a) and (b) to obtain a free-flowing mixed powder.

12. A thermal storage unit which is activated by exposure to microwave energy, said thermal storage unit comprising:
(a) a microwave-transparent container; and,
(b) a thermal storage composition enclosed within said container; said thermal storage composition comprising: a mixture of
(1) a first powder comprising calcium silicate impregnated with a microwave-sensitive material; and,
(2) a second powder comprising calcium silicate impregnated with a phase-change material.

13. A thermal storage unit according to claim 12, wherein said microwave-sensitive material comprises water; and, said phase-change material comprises paraffin wax.

14. A thermal storage unit according to claim 12, wherein said thermal storage composition is a free-flowing powder.

15. A thermal storage unit according to claim 12, wherein said container comprises a flexible pouch.

16. A heating construction comprising:
(a) a microwave-transparent outer cover; and,
(b) a thermal storage unit activatable by exposure to microwave energy; said thermal storage unit being positioned within said outer cover; said thermal storage unit comprising:
(i) a microwave-transparent container; and,
(ii) a thermal storage composition within said container; said thermal storage composition comprising: a mixture of
(1) a first powder comprising calcium silicate impregnated with a microwave-sensitive material; and,
(2) a second powder comprising calcium silicate impregnated with a phase-change material.

17. A heating construction according to claim 16, wherein said microwave-sensitive material comprises water; and, said phase-change material comprises paraffin wax.

18. A heating construction according to claim 16, wherein said microwave-transparent outer cover comprises a seat cushion.

19. A heating construction according to claim 16, wherein said thermal storage composition is a free-flowing impregnated powder.

20. A process of storing thermal energy for release over a extended period of time, said process including a step of:
(a) exposing a thermal storage composition to microwave energy; said thermal storage composition comprising: a mixture of
(1) a first powder comprising calcium silicate impregnated with a microwave-sensitive material; and,
(2) a second powder comprising calcium silicate impregnated with a phase-change material;
(b) said step of exposing said thermal storage composition to microwave energy comprising exposing said thermal storage composition to microwave energy of approximate power and for a sufficient period of time to heat said thermal storage composition to a temperature above the melting point of said phase-change material and to melt said phase change material.

* * * * *